(12) United States Patent
Sestak et al.

(10) Patent No.: US 8,173,418 B2
(45) Date of Patent: May 8, 2012

(54) DEVICE FOR ACTIVATING A SELF-CONTAINED BIOLOGICAL INDICATOR

(75) Inventors: Joseph T. Sestak, Erie, PA (US); Peter J. Buczynski, Girard, PA (US)

(73) Assignee: American Sterilizer Company, Mentor, OH (US)

( * ) Notice: Subject to any disclaimer, the term of this patent is extended or adjusted under 35 U.S.C. 154(b) by 709 days.

(21) Appl. No.: 12/137,591

(22) Filed: Jun. 12, 2008

(65) Prior Publication Data

US 2009/0311739 A1 Dec. 17, 2009

(51) Int. Cl.
*C12M 3/00* (2006.01)
*C12Q 1/24* (2006.01)

(52) U.S. Cl. ............... 435/287.6; 435/287.1; 435/287.4; 435/288.1; 435/31; 435/304.1; 422/401; 215/219

(58) Field of Classification Search ............... 435/287.1, 435/31, 287.4, 287.6, 288.1, 304.1, 400; 422/401; 215/219
See application file for complete search history.

(56) References Cited

U.S. PATENT DOCUMENTS

| | | | | |
|---|---|---|---|---|
| 1,353,719 A | 9/1920 | Buresch | | 72/400 |
| 2,466,907 A | 4/1949 | Nadolny et al. | | 153/10.5 |
| D196,726 S | 10/1963 | Bull | | D16/3 |
| 3,314,272 A | 4/1967 | Dahl | | 72/325 |
| 3,776,129 A | 12/1973 | Carlson | | 100/98 |
| 4,304,869 A | 12/1981 | Dyke | | 435/296 |
| 4,637,139 A | 1/1987 | Chen | | 30/164.9 |
| 4,732,850 A | 3/1988 | Brown et al. | | 435/31 |
| 5,256,537 A | 10/1993 | Phillips et al. | | 435/7.1 |
| 5,500,184 A | 3/1996 | Palmer | | 422/2 |
| 5,552,320 A | 9/1996 | Smith | | 435/287.4 |
| 5,710,041 A | 1/1998 | Moorman et al. | | 435/287.6 |
| 6,355,448 B1 | 3/2002 | Foltz et al. | | 435/31 |
| 6,566,090 B2 | 5/2003 | Witcher et al. | | 435/31 |
| 6,924,139 B2 | 8/2005 | Eveland et al. | | 435/287.4 |
| 7,563,616 B2 | 7/2009 | Gillis et al. | | 435/287.4 |
| 2005/0014214 A1 | 1/2005 | Eveland et al. | | 435/29 |
| 2006/0263258 A1 | 11/2006 | Harris et al. | | 422/99 |
| 2007/0077615 A1 | 4/2007 | Gillis | | 435/31 |
| 2008/0070272 A1 | 3/2008 | Franciskovich et al. | | 435/31 |
| 2008/0131971 A1 | 6/2008 | Clawson | | 436/66 |

FOREIGN PATENT DOCUMENTS

EP 0 152 298 8/1985

*Primary Examiner* — Nathan Bowers
*Assistant Examiner* — Gautam Prakash
(74) *Attorney, Agent, or Firm* — Kusner & Jaffe; Michael A. Centanni

(57) ABSTRACT

The present invention provides a device for activating a self-contained biological indicator. The biological indicator includes a casing, an ampule having a growth-promoting medium disposed therein and microorganisms. The ampule and microorganisms are disposed within the casing. The device is comprised of a first lever arm having a cavity formed therein. The cavity is dimensioned to receive a biological indicator. A second lever arm has a protrusion extending from a surface thereof and is moveable relative to the first lever arm to deform a casing of the biological indicator thereby fracturing an ampule in the casing and exposing microorganisms in the casing to a growth-promoting medium in the ampule of the biological indicator.

4 Claims, 4 Drawing Sheets

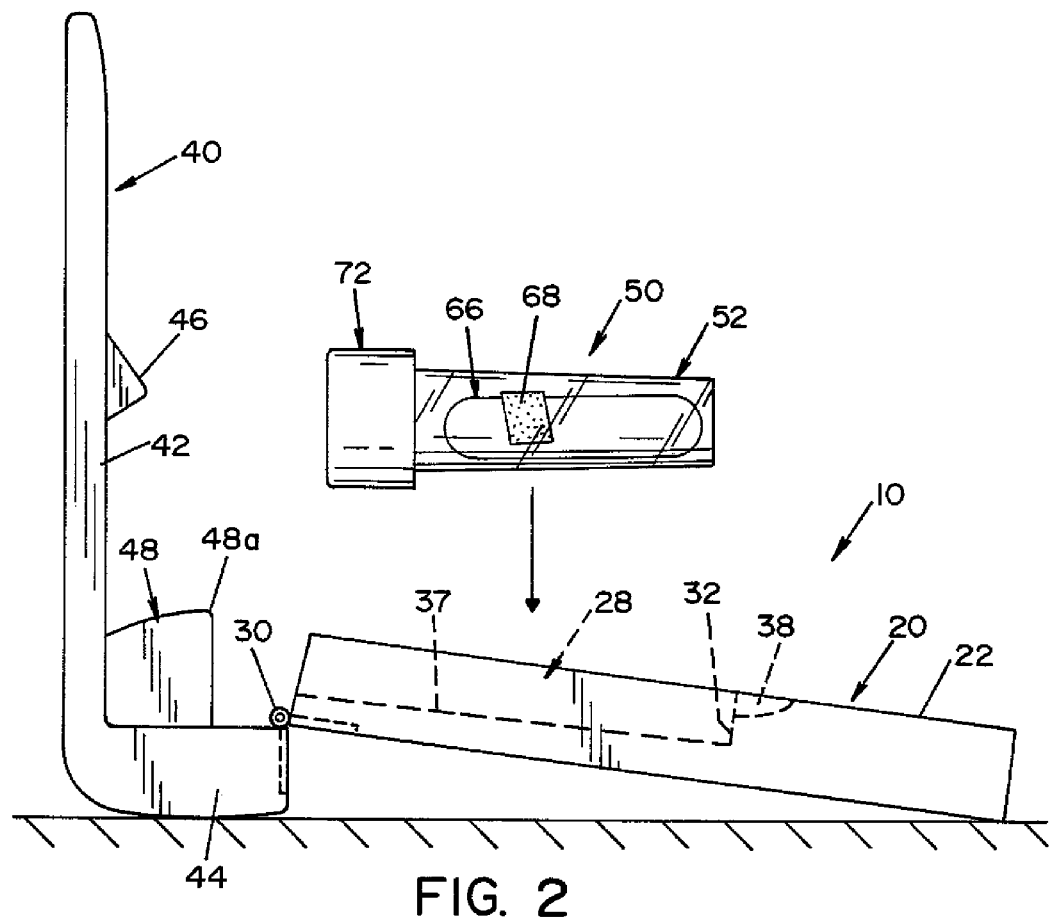
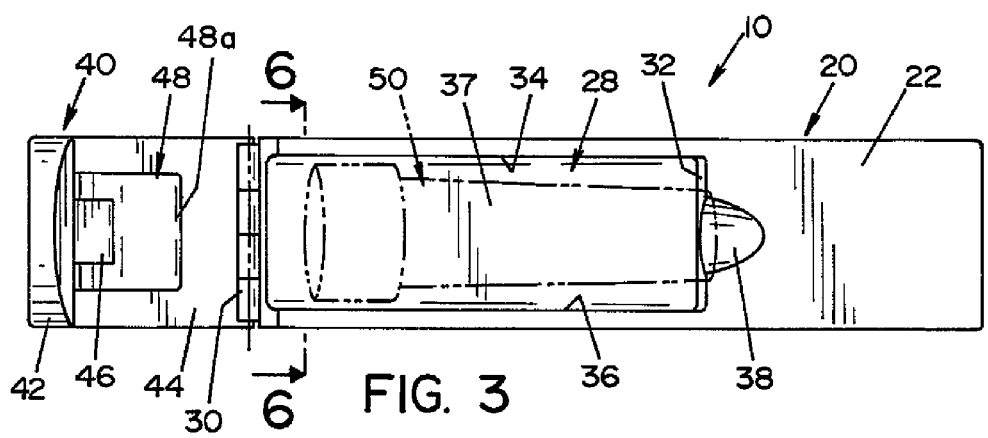

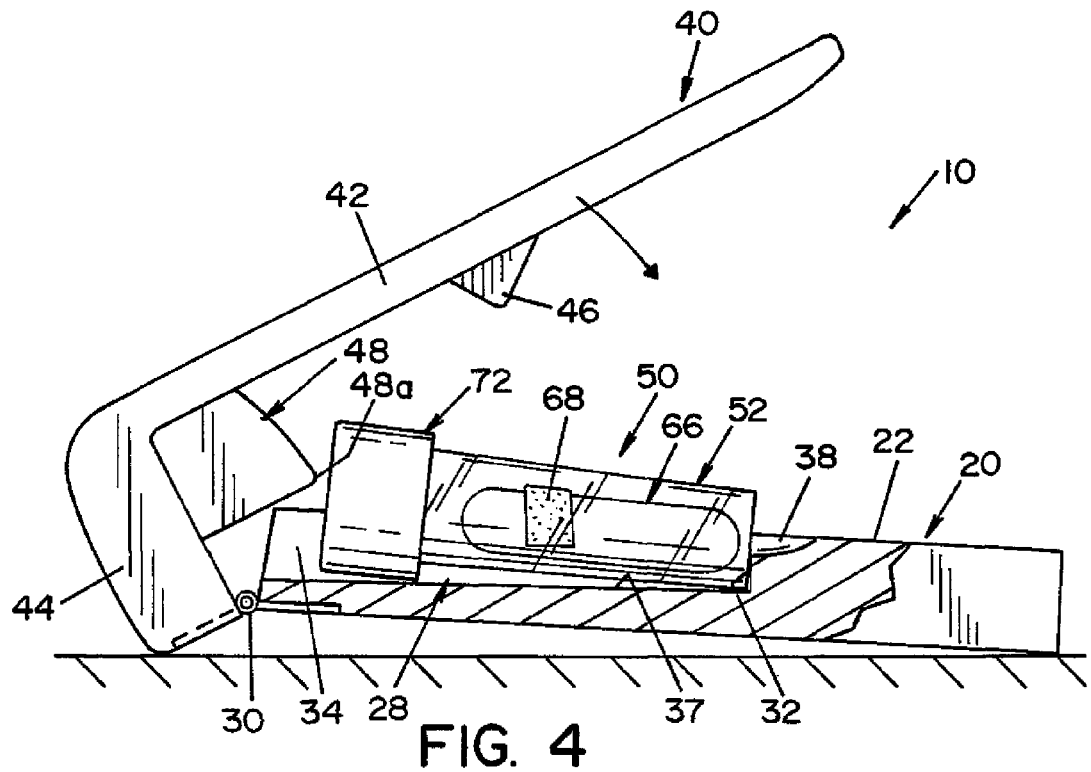
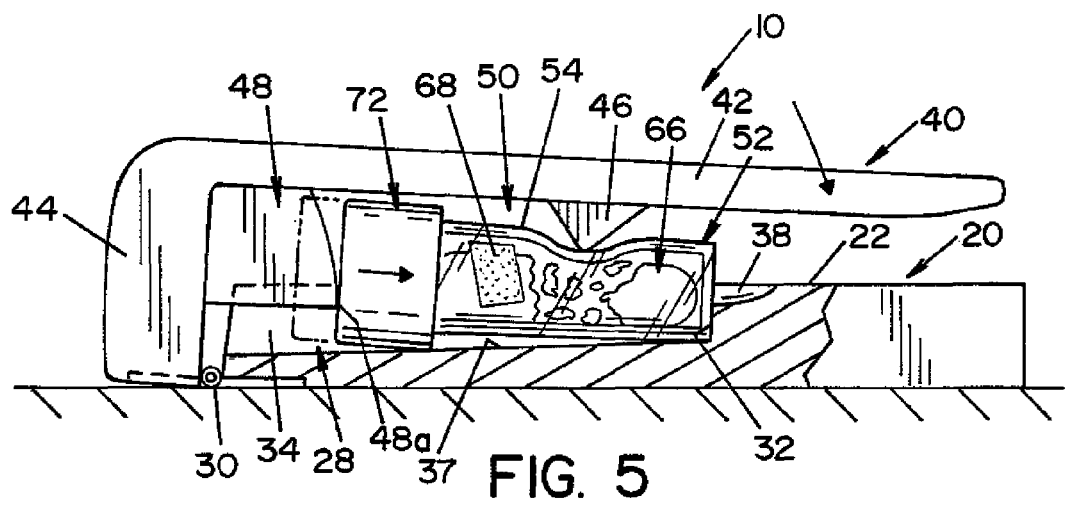
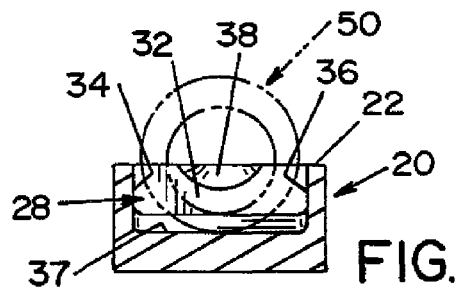

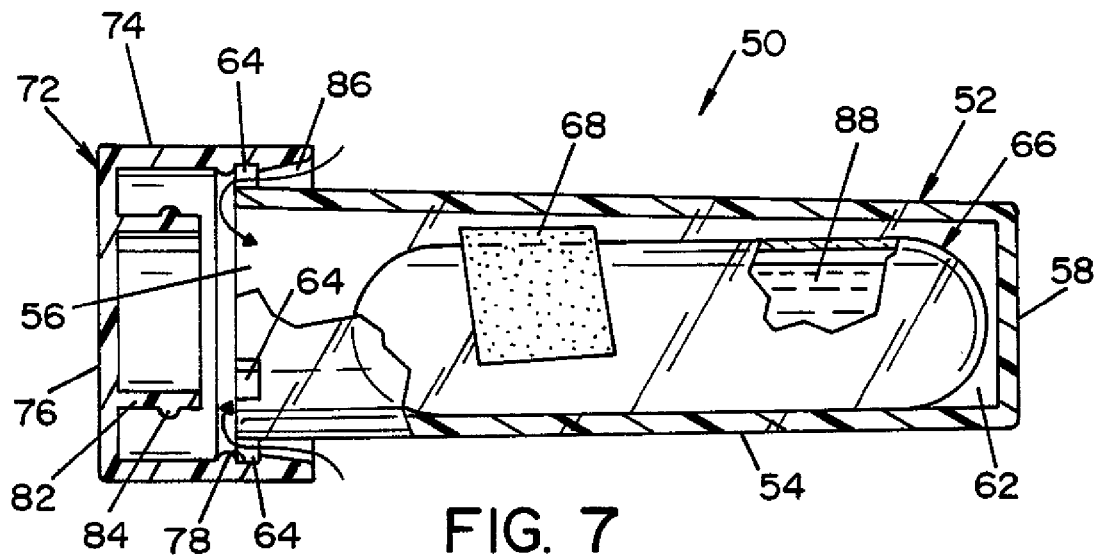
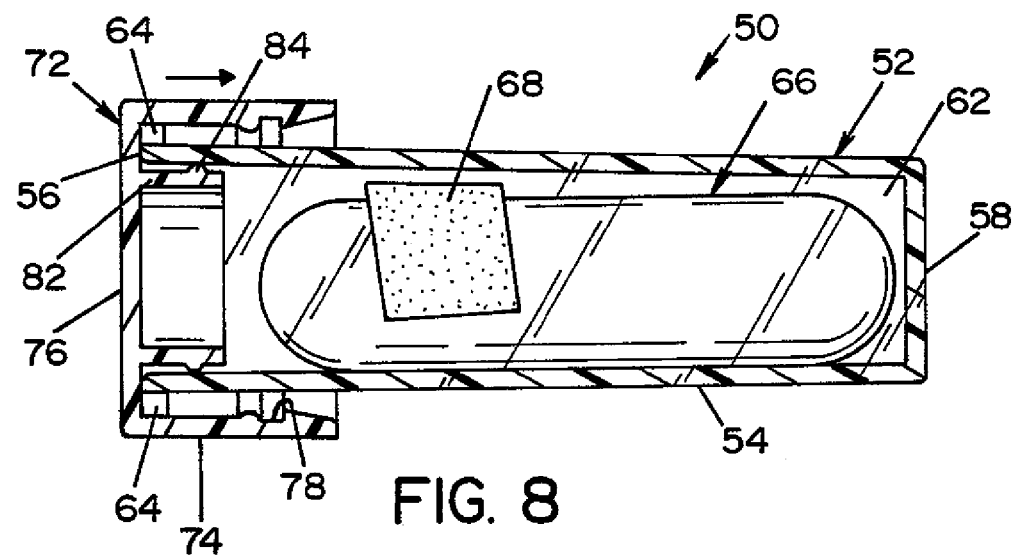

DEVICE FOR ACTIVATING A SELF-CONTAINED BIOLOGICAL INDICATOR

FIELD OF THE INVENTION

The present invention relates to self-contained biological indicators for evaluating the efficacy of a sterilization process, and more particularly, to a device for activating a self-contained biological indicator.

BACKGROUND OF THE INVENTION

Sterilization is a process conducted in a specially designed chamber or sterilizer that results in a complete eradication of all viable microorganisms. Sterilization techniques have evolved over time from the traditional methods employing saturated steam at elevated temperature and ethylene oxide gases to more modern techniques, such as those employing liquid, vapor and plasma. Regardless of the technique utilized, the effectiveness of the applied sterilization process must be evaluated especially when sterilizing instruments and devices invasive to the human body.

Several methods are currently available for evaluating the effectiveness of a sterilization process. In some applications, chemical indicators are placed in the sterilization process to verify that the sterilizing medium was present in the correct concentration during the sterilization process. In other applications, process indicators are used to determine if the sterilizing medium was present in the correct concentration for the proper amount of time. Still other applications use biological indicators to determine if the sterilizing medium was sufficient to deactivate a predetermined number of microorganisms on a test strip or contained in the biological indicator.

The biological indicator is typically an absorbent paper strip that contains a predetermined number of microorganisms. The biological indicator is exposed to the sterilizing medium during the sterilization process. At the conclusion of the sterilization process, the biological indicator is placed into a vial containing a growth-promoting medium, i.e., nutrients that aid in the growth of the microorganism. If there are any viable microorganisms on the paper strip that survived the sterilization process, these microorganisms will grow and produce a color change in the growth-promoting medium when properly incubated. The sterilization process is determined to be successful if there is no color change in the growth-promoting medium. In one embodiment, the biological indicator and the growth-promoting medium are disposed in a common housing. The combination of biological indicator and the growth-promoting medium in a common housing is often called a "self-contained biological indicator" (SCBI).

Self-contained biological indicators are generally comprised of a tubular housing having an open end and a closed end. A vial containing a growth-promoting medium is disposed in the housing. A source of microorganisms is also disposed in the housing. The source of microorganisms is typically an absorbent paper strip that has been impregnated with a pre-determined concentration of viable microorganisms. The microorganisms may also be disposed directly on the exterior surface of the vial. A cap is disposed over the open end of the housing. The cap is operable to move between an open position and a closed position. When the cap is in the open position, the interior of the housing is in fluid communication with the environment. In this respect, a sterilizing medium is able to flow into the interior of the housing and contact the source of microorganisms during the sterilization process. The self-contained biological indicator is removed from the chamber of the sterilizer at the end of the process. The cap is then moved to a closed position wherein the interior of the housing is fluidly isolated from the environment. Once sealed, the source of microorganisms is exposed to the growth-promoting medium by fracturing or breaking the vial containing the growth-promoting medium. The SCBI is then incubated at a predetermined temperature for a predetermined duration. At the end of the incubation period, the indicator is evaluated either visually or with a detector to determine whether any microorganisms survived the sterilization process.

As described above, the source of microorganisms is exposed to the growth-promoting medium. In order to expose the source of microorganisms to the growth-promoting medium, the vial must be fractured by the user. Presently, the user must exert a significant amount of force to the housing of the biological indicator to fracture the vial dispose therein. In some instances, the user may use a blunt instrument, e.g., a hammer, to fracture the vial. As a result, significant damage may occur to the biological indicator if excessive force is used. In this respect, present devices are complicated and may require multiple operations to seal and activate the biological indicator.

The present invention provides a device wherein a self-contained biological indicator for determining the efficacy of a sterilization process can be activated.

SUMMARY OF THE INVENTION

In accordance with a preferred embodiment of the present invention, there is provided a device for activating a self-contained biological indicator. The biological indicator includes a casing, an ampule having a growth-promoting medium disposed therein and microorganisms. The ampule and microorganisms are disposed within the casing. The device is comprised of a first lever arm having a cavity formed therein. The cavity is dimensioned to receive a biological indicator. A second lever arm has a protrusion extending from a surface thereof and is moveable relative to the first lever arm to deform a casing of the biological indicator thereby fracturing an ampule within the casing and exposing microorganisms within the casing to a growth-promoting medium disposed in the ampule.

In accordance with yet another embodiment of the present invention, there is provided a method of activating a self-contained biological indicator in a device. The biological indicator includes a casing, an ampule having a growth-promoting medium disposed therein and microorganisms. The ampule and microorganisms are disposed within the casing. The method is comprised of the steps of:

a) moving a device comprised of a first lever arm and a second lever arm to an open position, wherein the first lever arm is moveable relative to the second lever arm;

b) locating a biological indicator in a cavity located in the first lever arm of the device while the device is in the open position; and c) moving the device to a closed position by moving the second lever arm relative to the first lever arm such that a protrusion on the second lever arm fractures an ampule within the biological indicator thereby allowing a growth-promoting medium within the ampule to be exposed to microorganisms disposed in a casing of the biological indicator.

An advantage of the present invention is the provision of a device for activating a biological indicator.

Another advantage of the present invention is the provision of a device that seals a self-contained biological indicator prior to activating the self-contained biological indicator.

Still another advantage of the present invention is the provision of a device, as described above, that requires a simple operation to seal and activate a self-contained biological indicator.

Still another advantage of the present invention is the provision of a device, as described above, that is inexpensive to manufacture.

Yet another advantage of the present invention is the provision of a device, as described above, that allows hand-held operation.

Yet another advantage of the present invention is the provision of a device, as described above, that can be operated with one hand.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 2 is a side plan view of the device and biological indicator shown in FIG. 1;

FIG. 3 is a top plan view of the biological indicator shown in FIG. 2, wherein the biological indicator is shown in phantom inside the device;

FIG. 4 is a side plan view partially in section of the device for sealing and activating a biological indicator, wherein the device is shown in a partially open position with a biological indicator located inside the device;

FIG. 5 is a side plan view partially in section of the device shown in FIG. 4, wherein the device is shown in a closed position;

FIG. 6 is a sectional view taken along lines 6-6 of FIG. 3;

FIG. 7 is a sectional view of a biological indicator showing a cap of the biological indicator in an unsealed or open position; and FIG. 8 is a sectional view of the biological indicator shown in FIG. 7, showing the cap of the biological indicator in a sealed or closed position.

DETAILED DESCRIPTION OF THE PREFERRED EMBODIMENT

Figure 1:
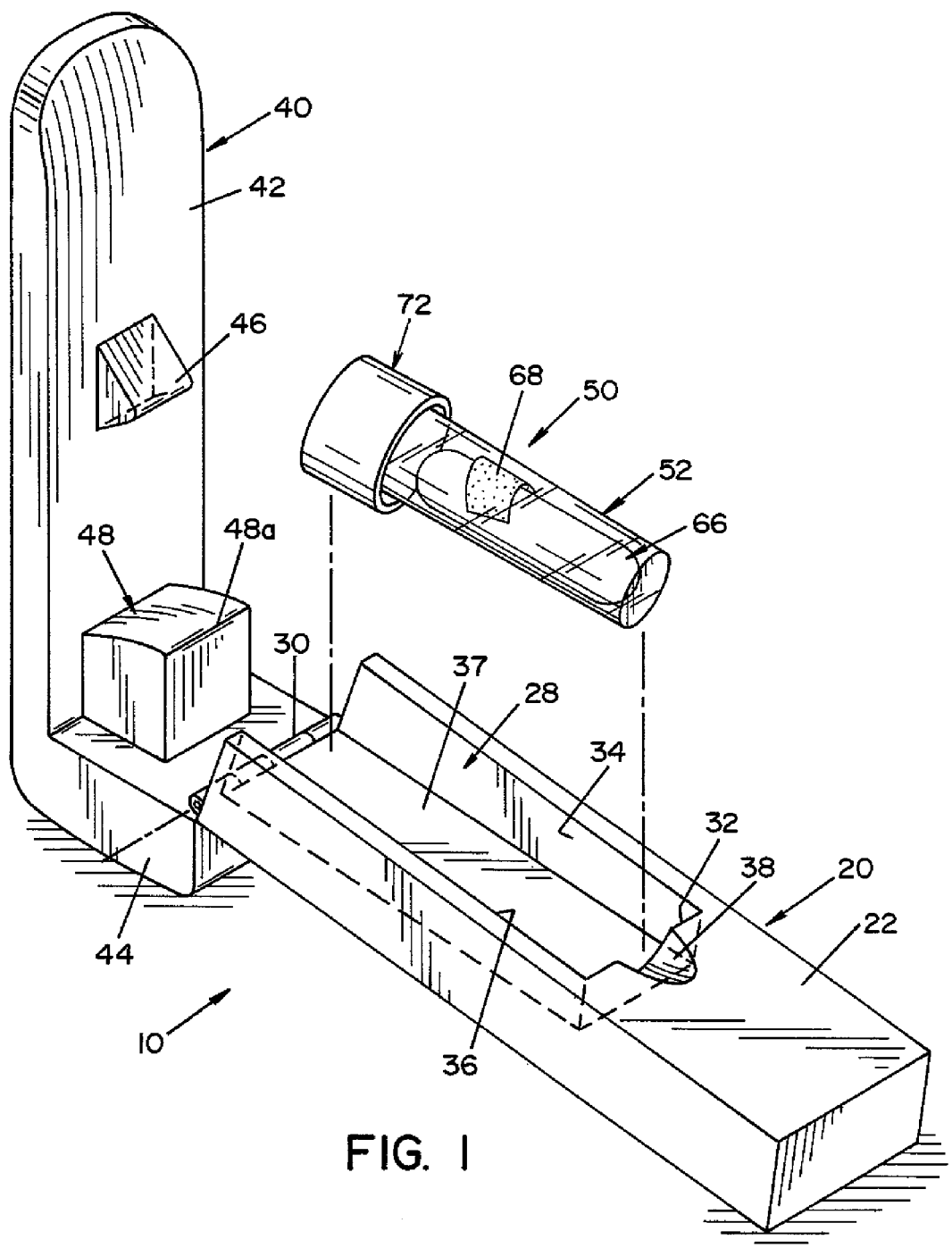
FIG. 1 is a perspective view of a device for sealing and activating a self-contained biological indicator according to an embodiment of the present invention, wherein the device is shown in an open position with a biological indicator located outside the device.

Referring now to the drawings wherein the showings are for the purpose of illustrating an embodiment of the invention only, and not for the purpose of limiting same. FIGS. 7 and 8 show a typical self-contained biological indicator 50 that is used in connection with device 10. Broadly stated, biological indicator 50 is comprised of a casing 52, a cap 72, an ampule 66 and a microorganism-inoculated element 68. It should be understood that indicator 50 is merely exemplary of a biological indicator suitable for use in connection with the present invention, and is not intended to limit the scope of the present invention.

Casing 52 is a generally cylindrical container having a cylindrical side wall 54, an open end 56 and a closed end 58. Casing 52 defines an interior cavity 62 dimensioned to receive ampule 66 and microorganism-inoculated element 68. A series of tabs 64 extend radially outward from side wall 54 near open end 56. The material for casing 52 is chosen such that when side wall 54 of casing 52 is subjected to a force, side wall 54 will deform but not fracture. Casing 52 is preferably formed of a translucent, polymer material, such as by way of example and not limitation, polypropylene, polyethylene, polycarbonate, polyvinyl carbonate, polyvinyl styrene, polyvinyl acetate, polymethylmethacrylate or any copolymers of the above materials.

Ampule 66 is a sealed enclosure formed from a frangible material, such as glass or other suitable materials, that allows ampule 66 to be opened by applying an external force sufficient to fracture or break ampule 66, as shall be described in greater detail below. It shall be appreciated that ampule 66 may assume shapes that differ from the shape illustrated herein. A growth-promoting medium 88 is disposed within ampule 66. Growth-promoting medium 88 is well known to those skilled in the art, and therefore shall not be described in detail. Examples of commonly used growth-promoting mediums include, but are not limited to, trypic soy broth and soybean casein digest growth media.

In the illustrated embodiment, microorganism-inoculated element 68 is a paper patch inoculated with spores or other microorganisms, as is conventionally known in the art. Microorganism-inoculated element 68 may be attached to the inner surface of casing 52, but in the embodiment shown, element 68 is affixed to an outer surface of ampule 66. In an alternative embodiment (not shown), the microorganisms are disposed directly on the exterior surface of ampule 66 or on the interior surface of casing 52.

Cap 72 is generally cup-shaped and includes a cylindrical side wall 74 and an end wall 76. A ring-shaped boss 82 extends inward from end wall 76. Boss 82 is centrally located on cap 72. An annular protrusion 84 extends radially outward from boss 82 near a distal end thereof. An annular groove 78 is formed in side wall 74 near an open end of cap 72. Annular groove 78 is dimensioned to accept tabs 64 of casing 52, as best seen in FIG. 7. An opening 86 is formed between casing 52 and cap 72, as best seen in FIG. 7, when tabs 64 are disposed in groove 78.

Cap 72 is movable between an unsealed or open position, best seen in FIG. 7, and a sealed or closed position, best seen in FIG. 8. In the open position, tabs 64 of casing 52 are disposed in annular groove 78 of cap 72. In this respect cavity 62 of casing 52 is in fluid communication with the exterior of indicator 50 through opening 86. In the sealed position, boss 82 of cap 72 is disposed in open end 56 of casing 52 such that annular protrusion 84 sealingly engages side wall 54 of casing 52. In this respect, a seal is formed between cap 72 and casing 52, thereby isolating cavity 62 from the exterior of indicator 50.

FIG. 1 shows a device 10 for activating a self-contained biological indicator (such as indicator 50 described above) in accordance with an embodiment of the present invention. Device 10 is described herein in connection with the sealing and activation of indicator 50. However, it is contemplated that device 10 may be used to seal and activate biological indicators of alternative designs.

Broadly stated, device 10 is comprised of a first lever arm 20 and a second lever arm 40. In the illustrated embodiment, a hinge member 30 connects a distal end of first lever arm 20 to a distal end of second lever arm 40 such that second lever arm 40 is rotatable relative to first lever arm 20. Second lever arm 40 is rotatable such that device 10 is movable between an open position and a closed position, as shall be described in greater detail below. It will be appreciated that first lever arm 20 and second lever arm 40 may be connected with each other by means other than hinge member 30. For example, first lever arm 20 and second lever arm 40 may be molded such that an integral hinge is formed therebetween.

In the embodiment shown, first lever arm 20 is an elongated rectangular member with a top surface 22. A cavity 28 is formed in top surface 22, as best seen in FIG. 1. Cavity 28 is defined by end surface 32, side walls 34, 36 and bottom surface 37. Cavity 28 is dimensioned to accept a biological indicator, such as indicator 50 described above. In the illustrated embodiment, a recess 38 is formed proximate one end of cavity 28, as best seen in FIG. 1. Recess 38 is dimensioned to facilitate the removal of indicator 50 from cavity 28, as shall be described in greater detail below.

In the embodiment shown, second lever arm 40 is a generally L-shaped member having an elongated first portion 42 and a shorter second portion 44 that is substantially perpendicular to first portion 42. A protrusion 46 extends from first portion 42, as shown in FIG. 1. In the embodiment shown, protrusion 46 is a generally triangular-shaped member that extends outward from first portion 42. Protrusion 46 is located along first portion 42 such that protrusion 46 aligns with cavity 28 when device 10 is in the closed position.

A cam member 48 is disposed at a corner where first portion 42 meets second portion 44. In the embodiment shown, cam member 48 is a generally rectangular element that extends outwardly from first portion 42 and second portion 44. An engaging surface or edge 48a of cam member 48 faces cavity 28.

Device 10 is operable to be moved between the open position, best seen in FIGS. 1 and 2, and the closed position, best seen in FIG. 5. In the open position, first lever arm 20 and second lever arm 40 are disposed such that cavity 28 in first lever arm 20 is accessible. In the closed position, edge 48a of cam member 48 is partially disposed in cavity 28 of first lever arm 20 and protrusion 46 aligns with and extends into cavity 28, as best seen in FIG. 5. In the embodiment shown, first lever arm 20 and second lever arm 40 are substantially parallel when device 10 is in the closed position.

Operation of device 10 will now be described in connection with the sealing and activation of a biological indicator (such as indicator 50). Indicator 50 is sealed and activated using device 10 following the use of indicator 50 in a sterilizer. In this respect, indicator 50 is placed within a chamber of a sterilizer (not shown) along with objects to be sterilized. Cap 72 of indicator 50 is in the unsealed or open position, as illustrated in FIG. 7. During a sterilization cycle, the sterilant fluid (gas or liquid) that is used in the sterilizer flows through opening 86 between cap 72 and casing 52, and into cavity 62 of casing 52 where the sterilant fluid acts on the microorganism-inoculated element 68.

At the end of the sterilization cycle, indicator 50 is removed from the chamber of the sterilizer. Device 10 is moved to the open position by rotating second lever arm 40 away from first lever arm 20. Indicator 50 is then placed into cavity 28 of device 10, as shown in FIGS. 2, 3 and 6. As described above, cavity 28 of device 10 is dimensioned such that when indicator 50 is disposed in cavity 28, indicator 50 contacts end surface 32 of cavity 28, as best seen in FIG. 4. Device 10 is moved from the open position to the closed position by rotating second lever arm 40 toward first lever arm 20. As second lever arm 40 moves toward first lever arm 20, device 10 moves from the open position, to an intermediate position to a closed position. As device 10 moves from the open position to the intermediate position, edge 48a of cam member 48 moves into cavity 28. Accordingly, indicator 50 is captured between cam member 48 and end surface 32. Edge 48a of cam member 48 initially contacts or engages cap 72 of indicator 50 as first lever arm 20 and second lever arm 40 move towards each other. As second lever arm 40 continues to move toward first lever arm 20, the distance between edge 48a of cam member 48 and end surface 32 decreases thereby causing the distance between cap 72 of indicator 50 and closed end 58 of indicator 50 to decrease. As cap 72 moves toward closed end 58, a first compressive force is applied to indicator 50 thereby causing cap 72 of indicator 50 to move from the unsealed or open position, best seen in FIG. 7, to the sealed or closed position, best seen in FIG. 8. Device 10 is in the intermediate position once cap 72 is in the sealed or closed position. In other words, cam member 48 is dimensioned such that when device 10 is in the intermediate position, the distance between engaging surface or edge 48a of cam member 48 and end surface 32 is equal to or less than the height of self-contained biological indicator 50 in the sealed or closed position. As a result, indicator 50 is sealed by device 10 when device 10 is in the intermediate position.

As second lever arm 40 continues to move relative to first lever arm 20, device 10 moves from the intermediate position to the closed position. As device 10 moves from the intermediate position to the closed position, protrusion 46 moves toward cavity 28 in first lever arm 20. Protrusion 46 initially contacts side wall 54 of casing 52. As second lever arm 40 continues to move toward first lever arm 20, protrusion 46 exerts a second, compressive force on side wall 54 of casing 52. Protrusion 46 is dimensioned such that the second, compressive force exerted on side wall 54 of casing 52 causes side wall 54 to deform and apply a compressive force to ampule 66 sufficient to fracture or break ampule 66, as shown in FIG. 5. Device 10 is in the closed position when ampule 66 is fractured by protrusion 46. As a result, microorganism-inoculated element 68 is exposed to growth-promoting medium 88 within ampule 66.

The sealing of casing 52 and fracturing of ampule 66 basically "activates" indicator 50 by exposing microorganism-inoculated element 68 to medium 88. Once activated, device 10 is moved to the open position and indicator 50 is removed from device 10. Recess 32 is dimensioned to allow an operator's finger to grip closed end 58 of indicator 50. In this respect, recess 32 is dimensioned to allow an operator to squeeze closed end 58 and cap 72 between a thumb and an opposing finger to aid in the removal of indicator 50 from device 10. Indicator 50 is then placed in a conventional incubator (not shown) at a temperature and for a time suitable for growing the microorganism in growth-promoting medium 88.

The present invention thus provides a device for quickly and easily activating a self-contained biological indicator 50. As indicated above, the rotation of second lever arm 40 relative to first lever arm 20 first seals the self-contained biological indicator 50 then fractures ampule 66 disposed in casing 52.

In an alternative embodiment of the present invention (not shown), cam member 48 is omitted from device 10. In this embodiment, it is contemplated that a user manually seals indicator 50 prior to placing indicator 50 in device 10. Thereafter, device 10 is moved from an open position to a closed position to fracture ampule 66, thereby activating indicator 50. Once activated, device 10 is moved to the open position and indicator 50 is removed from device 10.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A device movable between an open position and a closed position for sealing and activating a self-contained biological indicator, said biological indicator including a casing and a cap disposed on said casing, said cap movable between an open position and a sealed position relative to said casing and said casing defining an interior cavity dimensioned to receive microorganisms and an ampule having a growth-promoting medium disposed therein, said device comprising:

a first lever arm having a cavity formed therein dimensioned to receive the biological indicator, said cavity defined by an end wall, at least two side walls and a bottom surface;

a L-shaped second lever arm comprising:

a first portion having a protrusion extending from a surface thereof, a second portion extending from an end of said first portion in a direction substantially perpendicular to said surface of said first portion, and an engagement element having an engaging edge, said engagement element disposed in a corner defined by said second portion and said first portion, wherein said protrusion is spaced a predetermined distance from said engagement element; and a hinge connected to an end of said first lever arm and to an end of said second portion of said second lever arm for moving said second lever arm relative to said first lever arm such that said device moves between said open position wherein said cavity in said first lever arm is accessible and said closed position wherein said surface of said first portion of said second lever arm is substantially parallel to said bottom surface of said cavity in said first lever arm, said hinge connected to said ends of said first and second lever arms such that a) a distance between said engaging edge of said engagement element and said end wall of said cavity in said first lever arm decreases as said second lever arm moves toward said first lever arm to move said device from said open position to said closed position, said engaging edge applying a compressive force to said cap of said biological indicator located in said cavity to move said cap to said sealed position, and b) said protrusion moves toward said bottom surface of said cavity in said first lever arm in a direction substantially perpendicular to said bottom surface of said cavity when said device is in said closed position, said protrusion deforming said casing of said biological indicator located in said cavity and fracturing said ampule within said casing to expose said microorganisms within said casing to said growth-promoting medium disposed in said ampule.

2. A device as defined in claim 1, wherein said protrusion is a generally triangular-shaped member.

3. A device as defined in claim 1, wherein said device is hand-held.

4. A device as defined in claim 1, wherein said first lever arm includes a recess formed therein near one end of said cavity.

\* \* \* \* \*